(12) United States Patent
Weibrecht

(10) Patent No.: US 9,968,309 B2
(45) Date of Patent: May 15, 2018

(54) METHOD AND A CORRECTION SYSTEM FOR CORRECTING TRACER-UPTAKE MEASUREMENTS

(75) Inventor: Martin Weibrecht, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 336 days.

(21) Appl. No.: 13/511,018

(22) PCT Filed: Dec. 1, 2010

(86) PCT No.: PCT/IB2010/055530
§ 371 (c)(1),
(2), (4) Date: May 21, 2012

(87) PCT Pub. No.: WO2011/070484
PCT Pub. Date: Jun. 16, 2011

(65) Prior Publication Data
US 2013/0024126 A1    Jan. 24, 2013

(30) Foreign Application Priority Data

Dec. 8, 2009    (EP) .................................... 09178287

(51) Int. Cl.
| | | |
|---|---|---|
| G01N 33/48 | (2006.01) | |
| A61B 6/03 | (2006.01) | |
| G06F 19/00 | (2018.01) | |
| G06T 7/00 | (2017.01) | |
| A61B 6/00 | (2006.01) | |

(52) U.S. Cl.
CPC .......... *A61B 6/037* (2013.01); *G06F 19/3456* (2013.01); *G06T 7/0014* (2013.01); *A61B 6/481* (2013.01); *G06T 2207/10104* (2013.01)

(58) Field of Classification Search
CPC ............................ G06F 19/3456; A61B 6/037
USPC .......................................................... 702/19
See application file for complete search history.

(56) References Cited

U.S. PATENT DOCUMENTS

| | | |
|---|---|---|
| 5,687,208 A | 11/1997 | Bae et al. |
| 2002/0010551 A1 | 1/2002 | Wang et al. |
| 2007/0066892 A1 | 3/2007 | Haras et al. |
| 2007/0167750 A1 | 7/2007 | Niethammer |
| 2008/0319305 A1 | 12/2008 | Martin et al. |
| 2009/0117044 A1 | 5/2009 | Hengerer et al. |
| 2009/0274358 A1 | 11/2009 | Flohr et al. |
| 2010/0054559 A1 | 3/2010 | Narayanan |
| 2010/0317967 A1 | 12/2010 | Carlsen et al. |
| 2013/0024126 A1 | 1/2013 | Welbrecht |

FOREIGN PATENT DOCUMENTS

| | | |
|---|---|---|
| JP | S62254733 A | 11/1987 |
| JP | 2003225234 A | 8/2003 |
| JP | 2006145281 A | 6/2006 |
| JP | 2007271428 A | 10/2007 |
| JP | 2008061766 A | 3/2008 |
| WO | 2008081365 A2 | 7/2008 |

OTHER PUBLICATIONS

Chen et al, "Modeling Spect Acquisition and Processing of Changing Radiopharmaceutical Distributions", IEEE Nucl. Sci. Symp. and Medical Imaging Conference, 2001, pp. 1366-1370.
Kersemans et al, "Influence of Sedation and Data Acquisition Method on Tracer Uptake in Animal Models: [123I]-2-IODO-L-;Hinylalanine in Pentobarbital-Sedated Tumor-Bearing Athymic Mice", Nuclear Medicine and Biology, vol. 33, No. 1, 2006, pp. 119-123.

*Primary Examiner* — Jerry Lin

(57) ABSTRACT

This invention relates to a method and a correction system for correcting tracer-uptake measurements for patient specific variations in the tracer-uptake. Input data are received about the patient and subsequently it is determining whether the received input data include tracer-impact data that impact the tracer-uptake measurements for the patient. In case the tracer-impact data are included in the input data a comparing is performed where the tracer-impact data are compared with pre-stored reference data that have associated thereto a correction indicator indicating an amount of deviation of the tracer-uptake measurement due to the tracer-uptake dependent data. The correction indicator of the pre-stored reference data that match with the tracer-impact data is then used to correct the tracer-uptake measurements for the patient.

13 Claims, 3 Drawing Sheets

METHOD AND A CORRECTION SYSTEM FOR CORRECTING TRACER-UPTAKE MEASUREMENTS

FIELD OF THE INVENTION

The present invention relates to a method and a correction system for correcting tracer-uptake measurements for patient specific variations in the tracer-uptake.

BACKGROUND OF THE INVENTION

In several cancer diseases, 2-[$^{18}$F]-Deoxy-D-Glucose (FDG) is applied for monitoring response to therapy. To this end, sequential studies are performed. The uptake of the lesions is determined in a baseline Positron Emission Tomography (PET) study prior to therapy. This uptake is compared to the lesion uptake during therapy. It has been shown that decreasing uptake correlates with better response to the applied therapy. Likewise, the same or even increased tracer-uptake correlates with poor response. Besides FDG, other tracers have been investigated as well, e.g. $^{18}$F-fluoromisonidazole ($^{18}$F-FMISO) and $^{18}$F-fluoro-L-thymidine ($^{18}$F-FLT). Also for these tracers, changes of the tracer-uptake can be correlated to outcome in order to predict response to therapy. Of course, contrast agents for other imaging modalities (SPECT, US, MR) may also be employed in therapy monitoring.

For all diagnostic and monitoring approaches, the clinical protocol applied in the imaging procedures is essential, because the tracer distribution and the lesion uptake are dynamic processes. Immediately after tracer injection, the tracer is found in the blood pool only. The uptake in the lesion increases over a certain period of time until a plateau is reached. After reaching the maximum, the tracer is washed out and the tracer concentration in the lesion decreases again. Depending on the tracer, the disease, and further aspects, the maximum uptake is reached at different times post injection (p.i.). For example, FDG peaks at about two hours p.i. while the maximum FMISO uptake is found after about four hours p.i. To assess response, the optimum measurement would have to be performed at the peak uptake. For logistical reasons, however, much shorter times are applied in clinical practice. For instance, FDG data are usually acquired at sixty or ninety minutes p.i. PET acquisitions are performed comparatively early in the uptake phase. Since there is still a significant slope in the uptake curve at this point in time, variations in the delay between injection and acquisition impact the measured uptake. To complicate matters, the treatment influences the uptake mechanisms so that the uptake curve during therapy may be different from baseline and cause variations in the uptake measurements which may even invalidate the data with regard to the intended comparison of baseline and monitoring scan.

US2007/0066892 discloses a method for providing tomographic pictures of a patient with the aid of a tomographic system by injecting the patient with tracers and subsequently determining temporal concentration profile of the tracers in at least one predetermined body region in at least one scanning plane. The drawback with this reference is that there is no consideration taken to added complexity caused by a variable delay between the tracer injection and the measurement of the lesion uptake.

The inventor of the present invention has appreciated that an improved tracer-uptake measurements is of benefit, and has in consequence devised the present invention.

SUMMARY OF THE INVENTION

An object of the invention is to provide a tracer-uptake correction method and a system that correct for variation in time between injection and acquisition.

According to a first aspect, the present invention relates to a method of correcting tracer-uptake measurements for patient specific variations in the tracer-uptake, comprising:

receiving input data about said patient including data indicating how tracer uptake values $(TUV)_{meas}$ varies with time $T_{meas}$, determining whether the received input data include tracer-impact data that impact the tracer-uptake measurements for said patient, selecting tracer-uptake reference data based upon said tracer impact data, comparing the tracer-uptake reference data with said tracer uptake values $(TUV)_{meas}$, and based on the comparing;

applying a correction of the tracer-uptake measurements for said patient.

Thus, a method is provided that corrects tracer-uptake measurements for patient specific variations in the tracer-uptake and thus allows for more reliable and comparable tracer-uptake data that may be used for example in the assessment of treatment response of a cancer patient.

In one embodiment, the step of determining whether the input data acquired from said patient include tracer-impact data includes comparing whether a measurement time value $T_{meas}$ matches a reference time value $T_{ref}$ for said reference data, said step of applying a correction being performed in case of non-match between $T_{meas}$ and $T_{ref}$ by means of:

calculating the ratio of a tracer uptake value $(TUV)_{meas}$ at $T_{meas}$ and a corresponding reference tracer uptake value $(TUV)_{ref}$ at $T_{meas}$, or calculating the difference between the tracer uptake value $(TUV)_{meas}$ and a corresponding reference tracer uptake value $(TUV)_{ref}$ at $T_{meas}$, where the calculated ratio or the calculated difference is applied to convert the value of $(TUV)_{meas}$ to a converted value $(TUV)_{meas-conv}$ at $T_{ref}$. This is of particular advantage when the patient has been e.g. undergone a Positron Emission Tomography (PET)-scans where the tracer uptake value $(TUV)_{meas}$ is to be compared with a reference value to interpret the results of the tracer uptake value. Accordingly, it is no longer necessary that the same post injection time is applied, e.g. precisely after 2 hours because the $(TUV)_{meas}$ will always be converted to new$(TUV)_{meas-conv}$ at a pre-fixed post injection time (p.i.). Thus, a reliable way is provided to comet the tracer-uptake measurements for the patient. It should be noted that this difference/ratio may be applied to any method of correction, for instance to retrieve a correction curve from the reference curves or from the linear approximations.

In one embodiment, said reference time $T_{ref}$ is the time where the associated tracer uptake value $(TUV)_{ref}$ is at maximum for said tracer-uptake reference data.

In one embodiment, the step of determining whether the input data acquired from said patient include tracer-impact data includes comparing whether a measurement time value $T_{meas}$ matches a previous measurement time value $T_{prev}$ from previous tracer-uptake measurement data for said patient, where said tracer-impact data is the difference between $T_{meas}$ and $T_{prev}$.

In one embodiment, said step of applying a correction being performed in case of non-match between $T_{meas}$ and $T_{prev}$ by means of:
- calculating the ratio of a tracer uptake value $(TUV)_{meas}$ and a corresponding reference tracer uptake value $(TUV)_{ref}$ at $T_{meas}$ or $T_{prev}$, or
- calculating the difference between the tracer uptake value $(TUV)_{meas}$ and a corresponding reference tracer uptake value $(TUV)_{ref}$ at $T_{meas}$ or $T_{prev}$, where the calculated ratio or the calculated difference is applied to convert the value of $(TUV)_{meas}$ to a converted value $(TUV)_{meas-conv}$ at $T_{prev}$, or to convert a previous tracer uptake value $(TUV)_{prev}$ at said $T_{prev}$ to a converted value $(TUV)_{prev-conv}$ at said $T_{meas}$. This is of particular advantage when the patient has as an example been undergoing two PET-scans with two weeks interval. Generally, in order to compare the FDG-PET study for a particular lesion, it is important to compare the tracer uptake values $(TUV)_{prev}$ and $(TUV)_{meas}$ for the same times post injection (p.i.). However, for these two PET scan due to some reasons the p.i. for the two PET-scans are different, e.g. the p.i. for the previous PET scan is $T_{prev}$=60 minutes and $T_{meas}$=90 minutes for the subsequent PET scan. This means that it is not possible to compare $(TUV)_{prev}$ and $(TUV)_{meas}$ together because this delay of the first measurement (previous) and the second measurement leads to a reduced uptake measurement. Since reduced tracer uptake is interpreted as response to therapy, this can lead to wrong interpretation of the results. Accordingly, by applying said converting where either $(TUV)_{meas}$ is converted to $(TUV)_{meas-conv}$ at $T_{prev}$ (or convert $(TUV)_{prev}$ to $T_{meas}$) it is possible to reference the tracer uptake measurement to a specific times post injection (p.i.) and thus provide means to perform such correction.

In one embodiment, the tracer-impact data include:
- medical data indicating the type of drugs the patient is being treated with,
- data indicating the medication of the patient,
- data indicating the type of tracer injected to the patient, said determination of whether the received input data include tracer-uptake data that impact the tracer-uptake measurements for said patient comprising determining whether said received input data about said patient include one or more of said data.

In one embodiment, said tracer-uptake reference data is a tracer-uptake reference curve. In another embodiment, the reference curve is normalized, e.g. the maximum value is 1.0.

In one embodiment, the step of selecting tracer-uptake reference data based upon said tracer impact data includes selecting a reference curve that substantially matches said tracer-uptake measurement data for said patient. Thus, a matching may be performed where it is checked whether the tracer-uptake measurement data match to a given reference curve. As an example, assume that $T_{meas}$ is 60 minutes, but that the peak value is after 120 minutes. By applying a reference curve that matches or substantially matches the tracer-uptake measurement data the process of applying a correction is simplified significantly since it is now possible to simply read out a converted value $(TUV)_{meas-conv}$ after 120 minutes.

In one embodiment, the step of selecting tracer-uptake reference data based upon said tracer impact data includes selecting a reference curve indicating the dynamical behavior in the presence of the tracer-impact data included in the input data. In that way, a corresponding reference curve is selected that gives a meaningful comparison to the tracer-uptake measurement data. As an example, the type of the tracer impacts the dynamical behavior of the tracer uptake. Thus, it is highly relevant to select a reference curve for a same type of tracer.

According to a second aspect, the present invention relates to a computer program product for instructing a processing unit to execute said method steps when the product is run on a computer.

According to a third aspect, the present invention relates to a correction system for correcting tracer-uptake measurements for patient specific variations in the tracer-uptake, comprising;
- means for receiving input data about said patient including data indicating how tracer uptake values $(TUV)_{meas}$ varies with time $T_{meas}$,
- a processor for determining whether the input data include tracer-impact data that impact the tracer-uptake measurements for said patient, a processor for selecting tracer-uptake reference data based upon said tracer impact data,
- a processor for comparing the tracer-uptake reference data with said tracer uptake values $(TUV)_{meas}$, and based on the comparing;
- a processor for applying a correction of the tracer-uptake measurements for said patient.

In one embodiment, the correction system further comprises storage means for storing said input data about said patient and said reference data.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
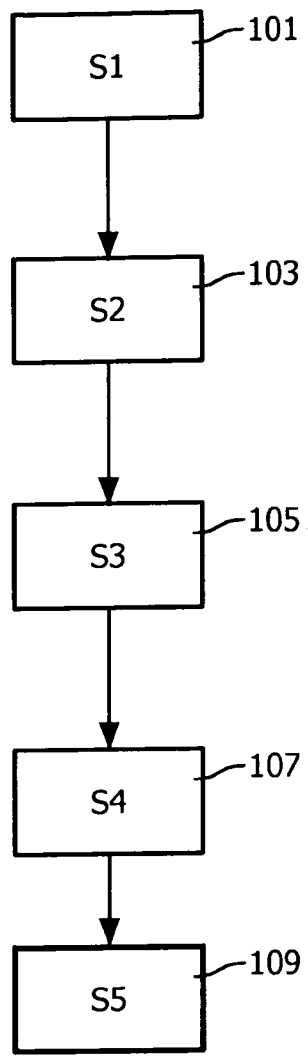
FIG. 1 shows a flowchart of an embodiment of the present invention of correcting tracer-uptake measurements for patient specific variations in the tracer-uptake.

FIG. 1 shows an embodiment of a flowchart of a method according to the present invention of correcting tracer-uptake measurements for patient specific variations in the tracer-uptake.

In step (S1) 101 input data is received about said patient including data indicating how tracer uptake values $(TUV)_{meas}$ varies with time $T_{meas}$. The input data may further include data received from e.g. a database that stores relevant information on individual patients, where this information may relate to disease and specific disease state, e.g. tumor staging, and the anticipated/running treatment approach as well as the state in the treatment course. The results of the investigations, e.g. location of lesions as well as volume and tracer uptake values (TUV) (in the praxis often referred to as standard-uptake value (SUV)) for each lesion as measured in prior studies may be stored as well. Additionally, the information may relate to the acquisition protocol by which these results have been obtained. Of special interest are the injected tracer activity and the delay between injection and acquisition. Also, the number of bed positions, the acquisition time per bed position, etc. may be of interest. The information may further comprise the patient's gender, the patient's size and weight as well as relevant in-vitro diagnostic information. For instance, insulin and glucose levels affect the FDG (2-[$^{18}$F]-Deoxy-D-Glucose) uptake.

Relevant information may be retrieved from Digital Imaging and Communications in Medicine (DICOM) tags present in image data such as injected activity, tracer, injection time, study time, scan direction, patient orientation, etc. Other information may be retrieved from other information systems in the hospital. In-vitro diagnostic data, for instance, may be accessible from a Laboratory Information System (LIS). Of course, information can also be entered by the clinicians.

In step (S2) 103, it is determined whether the received input data include tracer-impact data that impact the tracer-uptake measurements for said patient. The tracer-impact data can also be the type of drugs the patient is being treated with, other medication of the patient, the type of tracer or a combination thereof.

In step (S3) 105, tracer-uptake reference data are selected based upon said tracer impact data, where the tracer-uptake reference data can be a tracer-uptake reference curve which is preferable normalized.

In step (S4) 107, the tracer-uptake reference data are compared with said tracer uptake values $(TUV)_{meas}$, where based on the comparing a correction of the tracer-uptake measurements is applied for said patient (S5) 109.

In one embodiment, the step of determining whether the input data acquired from said patient include tracer-impact data includes comparing whether a measurement time value $T_{meas}$ matches a reference time value $T_{ref}$ for the reference data, or by comparing whether a measurement time value $T_{meas}$ matches a previous measurement time value $T_{prev}$ from previous tracer-uptake measurement data for the patient, where the tracer-impact data is the difference between $T_{meas}$ and $T_{prev}$.

In another embodiment, the step of determining whether the input data acquired from said patient include tracer-impact data includes comparing whether a measurement time value $T_{meas}$ matches a reference time value $T_{ref}$ for said reference data, where said step of applying a correction being performed in case of non-match between $T_{meas}$ and $T_{ref}$ by means of calculating the ratio of a tracer uptake value $(TUV)_{meas}$ at $T_{meas}$ and a corresponding reference tracer uptake value $(TUV)_{ref}$ at $T_{meas}$, where the calculated ratio is applied to convert the value of $(TUV)_{meas}$ to a converted value $(TUV)_{meas\text{-}conv}$ at $T_{ref}$. This may be considered as a linear transformation being performed on the tracer-uptake measurements, e.g. scale and/or offset, resulting in that the tracer-uptake measurements for said patient substantially matches said reference tracer uptake behavior (i.e. tracer uptake behavior in the absence of the tracer impact data) of the target lesion. In case of multiple lesions, a transformation may be determined for each lesion. Two cases should preferably be considered. If in the study only a single static acquisition has been performed, there is only a single uptake value per lesion. Therefore, the linear transformation becomes a single parameter: offset or scale factor (whatever is appropriate according to the model). If several acquisitions of the lesion have been performed, for instance by means of a dynamic study, an optimizer (e.g. least squares) can be used to determine an optimal linear transformation, which minimizes the error between the measured uptake values and the uptake values of the population mean model evaluated at the different acquisition delays of the dynamic study. The result is the desired output of the correction, namely the estimated uptake value at the reference acquisition delay. This will be discussed in more details later in relation to example 1 and FIG. 2.

Said step of applying a correction may also be done by calculating the difference between the tracer uptake value $(TUV)_{meas}$ and a corresponding reference tracer uptake value $(TUV)_{ref}$ at $T_{meas}$, where the calculated difference is applied to convert the value of $(TUV)_{meas}$ to a converted value $(TUV)_{meas\text{-}conv}$ at $T_{ref}$.

Begin Example 1

A patient has been diagnosed having lung cancer. The patient is sent to a FDG (2-[$^{18}$F]-Deoxy-D-Glucose)-PET study for staging, i.e. to look for distant metastases. Therefore a whole-body PET study covering head to thigh is to be done.

In whole-body PET imaging, imaging is performed in multiple bed positions because a PET system has limited axial coverage: the axial field-of-view for each bed position is about 20 cm, axial patient feed per bed position is about ~10 cm resulting in an overlap of the bed positions of ~10 cm.

The clinical protocol of the site foresees the start of the PET acquisition 60 minutes after injection of the tracer. According to the protocol, patients are asked to urinate 10 minutes before PET acquisition, i.e. 50 minutes after tracer injection, to empty the bladder in order to avoid image artifacts in the abdomen. Since the bladder fills again during imaging, imaging starts at the height of the thigh (first acquired bed position) and proceeds from there to the head to minimize bladder impact. The protocol foresees 2.5 minutes imaging time per bed position.

For the height of our specific lung cancer patient, 10 bed positions need to be acquired to cover the patient completely. Although the patient was asked to visit the restroom in time, the patient presents at the PET system 10 minutes late. Therefore, the acquisition does not start 60 min p.i. but only 70 min p.i. The actual lung tumor is imaged in the ninth bed position, i.e. 8*2.5 min=20 min. after the start of imaging. In total, the delays for imaging the tumor add up to 30 minutes, i.e. tumor tracer uptake is actually measured 90 minutes p.i.

The patient is lucky: no metastases were found. An induction-chemotherapy is applied to shrink the tumor before surgery. To determine response to the chemotherapy, a second FDG PET is performed three weeks after the first PET. This time, only one bed position at the tumor location is acquired. The patient does not need to urinate and presents in time for the acquisition. Hence, the second acquisition starts exactly 60 min. p.i.

Figure 2:
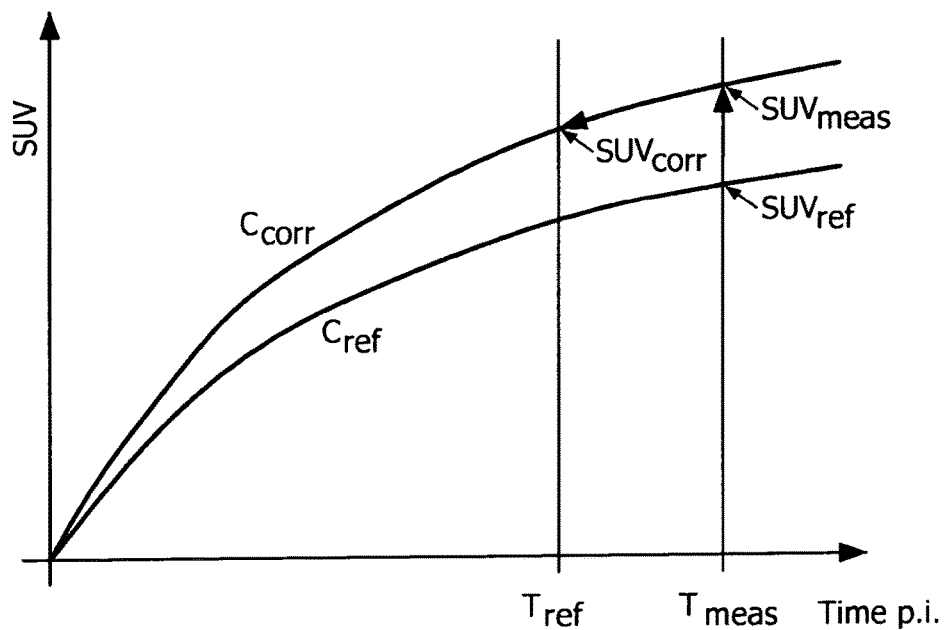
FIGS. 2 and 3 depicts graphically an example of tracer-uptake correction according to the present invention.

Since the tumor tracer uptake peaks at only about two hours p.i., the uptake at 60 min. p.i. is well below the maximum uptake and it is below the uptake at 90 min. p.i. The mere difference in the delay of the first measurement (i.e. $T_{prev}$) and the second measurement (i.e. $T_{meas}$) leads to a reduced uptake measurement. Since reduced tracer uptake is interpreted as response to therapy, this can lead to wrong interpretation of the results. Therefore, it is necessary that the tracer uptake measurement is referenced to a specific time p.i. which is solved via said method steps by performing said correction. FIG. 2 depicts graphically an example of a reference curve $C_{Ref}$ which has been normalized for a peak value of 1 (at about 2 h p.i.). The first measurement of the tumor was done 90 min. p.i.: at that time. For clarification, the tracer uptake values (TUV) may also be considered as a standard-uptake value, or (SUV). As depicted here, $SUV_{Ref}$ is 0.8 according to $C_{Ref}$. The actual measurement of the tumor uptake was $SUV_{meas}$=4. The resulting scale factor for $C_{Ref}$ to derive the correction curve $C_{corr}$ is 4/0.8=5. At the reference time $T_{Ref}$=60 min. the value of correction curve is only 75% of the value at $T_{meas}$=90 min, i.e. $SUV_{corr}$ becomes 3.

After correcting the tumor uptake for the time delay, the measured SUV of 4 is reduced to a SUV of 3 for the reference time of 60 min. Therefore, the second SUV measurement acquired at 60 min. p.i. must be less than 3 in order to indicate response to therapy (and not less than 4, the original first SUV)

End Example 1

Begin Example 2

Figure 3:
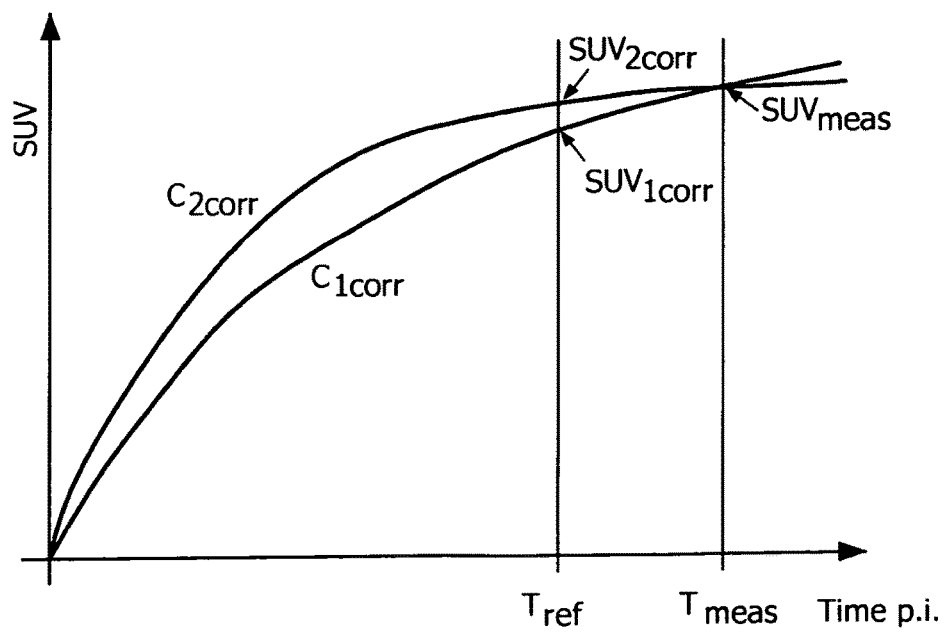

FIG. 3 depicts graphically another example of tracer-uptake correction according to the present invention, where as mentioned before in relation to FIG. 2 the x-axis stands for time and the y-axis for standard-uptake value (SUV). $C_{Ref}$ is not shown in FIG. 3 for simplicity reasons, but it has the same basic purpose as in FIG. 2, which is to be used as a first model of the tracer dynamics, except in this example additional data on the patient, which relate to information that has an effect on the tracer dynamic characteristics (tracer-impact data) is used when determining which reference curve ($C_{Ref}$) to use from the database. Such data may be insulin level, glucose level, treatment course and phase in treatment course, etc.

As mentioned before, various conditions have an effect on the uptake mechanisms. In the case of discrete conditions, for instance treatment with drug A, B, or C, individual curves/parameters can be used for each condition.

In case of effects associated with continuous parameters, for instance glucose levels in blood, two approaches are possible. Firstly, one may discretize the continuous parameter and create curves for each sample of the parameter. In the correction, one may use a nearest neighbor approach or interpolate between the two nearest neighbors. Secondly, one may describe the parameters of the mathematical function representing the tracer uptake as functions of the continuous parameters. For instance, if a linear approximation of the tracer uptake is employed, the slope parameter can be expressed as function of the glucose level (or any other continuous parameter affecting the slope). For this approach, the model would store the function parameters that are required to determine the model parameters instead of the model parameter.

As in the example depicted in FIG. 2, the actual measurement time ($T_{meas}$) is provided and a reference time ($T_{Ref}$) that is the intended measurement time. At the measurement time ($T_{meas}$), the tracer concentration is $SUV_{meas}$. The correction indicator is derived in the same ways as in the depicted example in FIG. 2, for example by adding the difference of the two values, $SUV_{meas}$-$SUV_{Ref}$ to $C_{Ref}$ while maintaining the origin at (0,0) fixed.

The correction, however, results in different correction curves ($C1_{corr}$ and $C2_{corr}$) and is the result from different tracer-impact dependent reference curves ($C_{Ref}$) selected as described above.

An example scenario of above described correction is the following; A patient gets injected with a tracer agent for examination purposes. If FDG is used as tracer agent, a peak in tracer agent concentration is achieved after approximately 120 min, but due to logistical or other unforeseen events the patient is measured by the PET-system after only 67 min. Before the procedure starts, relevant patient data is received by the system and determined if it comprises tracer impact data as in the depicted example in FIG. 2. In this scenario tracer impact data is found so the associated tracer impact parameters are then used for the selection of the appropriate reference curve model, $C_{Ref}$. As an example, after 67 min a measurement of the SUV is performed resulting in $SUV_{meas}$. Now, the tracer-impact data ($SUV_{meas}$) are compared with pre-stored reference data ($SUV_{Ref}$) having associated thereto a correction indicator or similar means. The correction indicator of pre-stored reference data that match with said tracer-impact data indicates the amount of deviation of the tracer-uptake measurement due to said tracer-uptake dependent data. The correction indicator is calculated for example by adding the difference of the two values, $SUV_{meas}$-$SUV_{Ref}$ to $C_{Ref}$ while maintaining the origin at (0,0) fixed. By applying a correction of the tracer-uptake measurements for said patient based on said correction indicator it results in a new correction curve ($C_{corr}$) of the tracer dynamics that is based on the actual measurement. Based on $C_{corr}$ the preferred reference time ($T_{Ref}$) can be selected and the correlating SUV, $SUV_{corr}$ can be derived. This makes it possible to compare measurements done at different times and compare the results to see possible progress in the treatment.

End Example 2

Figure 4:
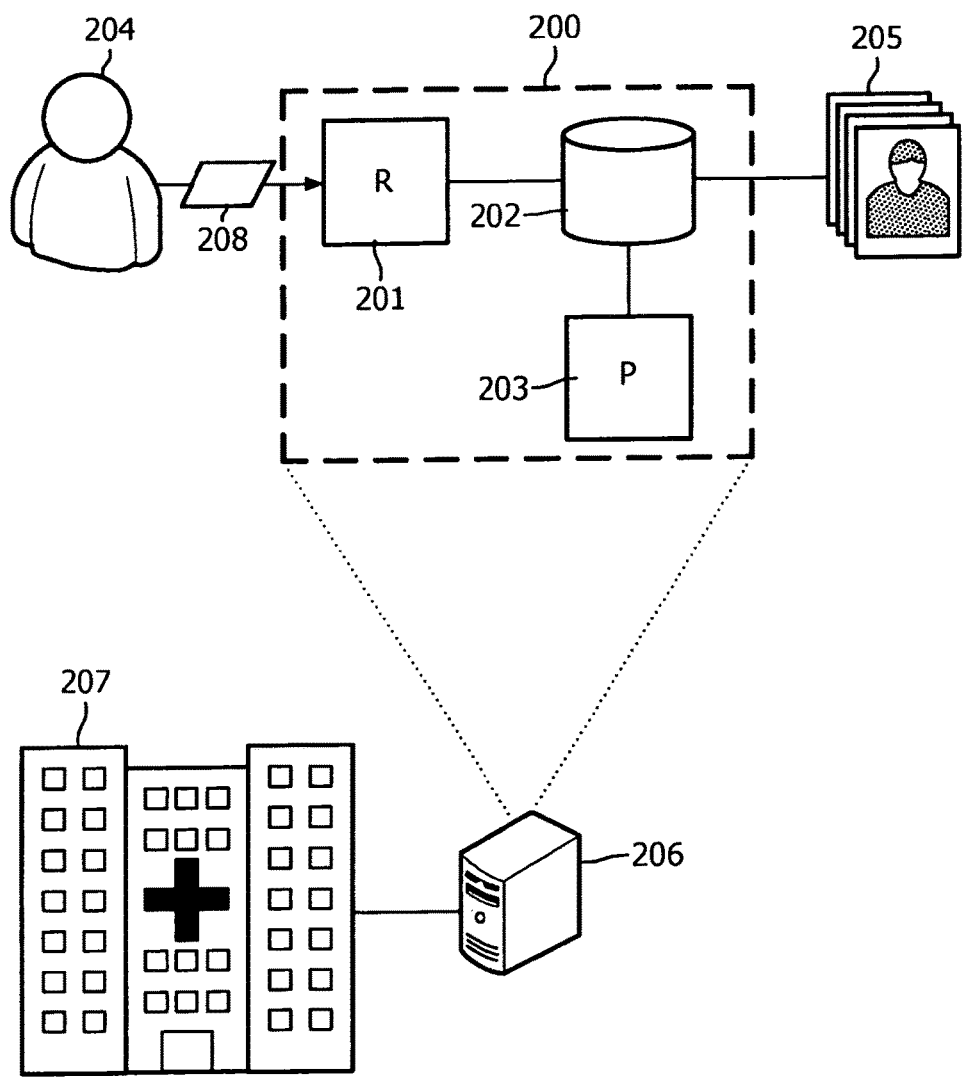
FIG. 4 shows an embodiment of a correction system for correction of tracer-uptake measurements for patient specific variations in tracer-uptake.

FIG. 4 shows an embodiment of a correction system 200 according to the present invention for correction of tracer-uptake measurements for patient 204 specific variations in tracer-uptake, where the system comprises means for receiving (R) input data 201 about the patient 204, a processor (P) 203 and storage means 202.

The means for receiving input data 208 may as an example be, and is not limited to, transceiver or a receiver that receives the data via a wired or wireless communication channel by accessing the database 208, or a CD drive where the patient input data 201 for a CD-ROM. The means for receiving input data 208 may also be a user-input interface that receives and stores information from a user, e.g. a mouse, a keyboard, a touch pad or a scanner and the like.

The processor (P) 203 is adapted to: i) determine whether the input data include tracer-impact data that impact the tracer-uptake measurements for said patient, ii) selecting tracer-uptake reference data based upon said tracer impact data, iii) comparing the tracer-uptake reference data with said tracer uptake values $(TUV)_{meas}$, and based on the comparing; iv) applying a correction of the tracer-uptake measurements for said patient.

The processor (P) 203 may be an integral part of a computer system 206 e.g. belonging to a clinical institute 207 that comprises said storage means stores, computes and communicates with other systems where the computing can as an example be performed by a central processing unit and a graphics processing unit. The storing can as an example be performed by any type of non-volatile memory and/or volatile memory, such as a hard drive, a USB key, a flash drive and a random access memory. The processor (P) 203 may be adapted to communicate with other systems having stored therein personal information including said reference data, an imaging system, such as a PET, SPECT, MRI, CT or any combination thereof. The processor (P) 203 may further be adapted to communicate with external computers and other systems adapted for communication in a hospital environment, such as laboratory information systems, digital imaging and communications in medicine systems, personal digital assistant, beepers and cell phones.

The storage means 202 may be adapted for, in addition to storing said data, sending and receiving patient's related information. The storage means 202 can for example store, send and receive information such as the personal information described above and/or the acquired above described input data about the patient and/or the above described reference data.

The correction system 200 may further comprise an image viewer (not shown) and tools to delineate target volumes in the acquired PET data. From the image data and the delineated regions, the parameters of interest, in particular the SUV's, are acquired. The viewer may also be able to display the results of the correction. Finally, the viewer may support visualization of image data and delineated regions as well as the measured and the corrected uptake values for several sequential studies. If more than two sequential studies have been performed, the viewer may depict the SUV data in graphics, again for the raw data as measured and for the data corrected as described.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items-recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of correcting tracer-uptake measurements for a patient, comprising:
    acquiring, by an image viewer, one or more images from a medical imaging modality,
    delineating, by the image viewer, target volumes from the acquired one or more images,
    acquiring input data about said patient from the delineated target volumes, including data indicating how tracer uptake values $(TUV)_{meas}$ varies with time $T_{meas}$,
    determining, by a processor, whether the input data includes tracer-impact data that impact the tracer-uptake measurements for said patient,
    selecting, by the processor, tracer-uptake reference data based upon said tracer impact data,
    comparing, by the processor, the tracer-uptake reference data with said tracer uptake values $(TUV)_{meas}$, and based on the comparing;
    applying, by the processor, a correction of the tracer-uptake measurements for said patient, and
    displaying, by the image viewer, a graphical representation of the input data and the correction of the tracer-uptake measurements.

2. A method according to claim 1, wherein the step of determining whether the input data acquired from said patient include tracer-impact data includes comparing whether a measurement time value $T_{meas}$ matches a reference time value $T_{ref}$ for said reference data, said step of applying a correction being performed in case of non-match between $T_{meas}$ and $T_{ref}$ by means of:
    calculating the ratio of a tracer uptake value $(TUV)_{meas}$ at $T_{meas}$ and a corresponding reference tracer uptake value $(TUV)_{ref}$ at $T_{meas}$, or
    calculating the difference between the tracer uptake value $(TUV)_{meas}$ and a corresponding reference tracer uptake value $(TUV)_{ref}$ at $T_{meas}$,
    where the calculated ratio or the calculated difference is applied to convert the value of $(TUV)_{meas}$ to a converted value $(TUV)_{meas\text{-}conv}$ at $T_{ref}$.

3. A method according to claim 2, wherein said reference time $T_{ref}$ is the time where the associated tracer uptake value $(TUV)_{ref}$ is at maximum for said tracer-uptake reference data.

4. A method according to claim 1, wherein the step of determining whether the input data acquired from said patient include tracer-impact data includes comparing whether a measurement time value $T_{meas}$ matches a previous measurement time value $T_{prev}$ from previous tracer-uptake measurement data for said patient, where said tracer-impact data is the difference between $T_{meas}$ and $T_{prev}$.

5. A method according to claim 4, wherein said step of applying a correction being performed in case of non-match between $T_{meas}$ and $T_{prev}$ by means of:
    calculating the ration of a tracer uptake value $(TUV)_{meas}$ and a corresponding reference tracer uptake value $(TUV)_{ref}$ at $T_{meas}$ or $T_{prev}$; or
    calculating the difference between the tracer uptake value $(TUV)_{meas}$ and a corresponding reference tracer uptake value $(TUV)_{ref}$ at $T_{meas}$ or $T_{prev}$,
where the calculated ratio or the calculated difference is applied to convert the value of $(TUV)_{meas}$ to a converted value $(TUV)_{meas\text{-}conv}$ at $T_{prev}$, or to convert a previous tracer uptake value $(TUV)_{prev}$ at said $T_{prev}$ to a converted value $(TUV)_{prev\text{-}conv}$ at said $T_{meas}$.

6. A method according to claim 1, wherein the tracer-impact data include:
    medical data indicating the type of drugs the patient is being treated with,
    data indicating the medication of the patient,
    data indicating the type of tracer injected to the patient,
    said determination of whether the received input data include tracer-uptake data that impact the tracer-uptake measurements for said patient comprising determining whether said received input data about said patient include one or more of said data.

7. A method according to claim 1, wherein said tracer-uptake reference data is a tracer-uptake reference curve.

8. A method according to claim 7, wherein the reference curve is normalized.

9. A method according to claim 7, wherein the step of selecting tracer-uptake reference data based upon said tracer impact data includes selecting a reference curve that substantially matches said tracer-uptake measurement data for said patient.

10. A method according to claim 7, wherein the step of selecting tracer-uptake reference data based upon said tracer impact data includes selecting a reference curve indicating the dynamical behavior in the presence of the tracer-impact data included in the input data.

11. A non-transitory computer readable storage medium storing instructions for instructing a processing unit to execute the method step of claim 1 when the product is run on a computer.

12. A correction system for correcting tracer-uptake measurements for patient specific variations in the tracer-uptake, comprising;
an image viewer for:
acquiring one or more images from a medical imaging modality;
delineating target volumes from the acquired one or more images,
acquiring input data about said patient from the delineated target volumes, including data indicating how tracer uptake values $(TUV)_{meas}$ varies with time $T_{meas}$, a processor for:
determining whether the input data include tracer-impact data that impact the tracer-uptake measurements for said patient,
selecting tracer-uptake reference data based upon said tracer impact data,
comparing the tracer-uptake reference data with said tracer uptake values $(TUV)_{meas}$, and based on the comparing;
applying a correction of the tracer-uptake measurements for said patient;
the image viewer displaying a graphical representation of the input data and the correction of the tracer-uptake measurements.

13. A correction system according to claim 12, further comprising a storage means for storing said input data about said patient and said reference data.

* * * * *